United States Patent [19]

Konoshima

[11] 4,110,820
[45] Aug. 29, 1978

[54] SPARE LAMP HOLDING DEVICE FOR A LIGHT SUPPLY DEVICE FOR ENDOSCOPE

[75] Inventor: Katunaga Konoshima, Tokyo, Japan

[73] Assignee: Olympus Optical Co., Ltd., Tokyo, Japan

[21] Appl. No.: 751,018

[22] Filed: Dec. 16, 1976

[30] Foreign Application Priority Data

Dec. 24, 1975 [JP] Japan ............................ 50-173691[U]

[51] Int. Cl.² .............................................. F21V 19/04
[52] U.S. Cl. ................................... 362/207; 362/184; 362/32
[58] Field of Search ............ 240/1 LP, 51.11 A, 2.18, 240/37, 41.15, 41.55, 90; 128/4, 6, 9; 362/184, 207, 227, 254, 362, 375, 32

[56] References Cited

U.S. PATENT DOCUMENTS

| 2,494,652 | 1/1950 | Ganzert ............................ 240/90 X |
| 3,195,536 | 7/1965 | Hovnanian et al. ..................... 128/6 |
| 3,529,149 | 9/1970 | Dwyer .................................... 240/90 |
| 3,638,013 | 1/1972 | Keller ............................ 240/1 LP X |
| 3,775,606 | 11/1973 | Bazell et al. ................... 240/1 LP X |

Primary Examiner—J D Miller
Assistant Examiner—Peter S. Wong

[57] ABSTRACT

A light supply device for endoscope in which a space defined adjacent to a light source section including a socket and a lamp attached thereto communicates with the outside through an opening. At the opening is swingably provided a cover hinge-coupled to the frame of the device at one end, while on the back of the cover is fixed a holder to which a spare lamp for replacement is removably fitted. The spare lamp is contained in the space when the cover is in the close position.

3 Claims, 3 Drawing Figures

SPARE LAMP HOLDING DEVICE FOR A LIGHT SUPPLY DEVICE FOR ENDOSCOPE

BACKGROUND OF THE INVENTION

The present invention relates to a spare lamp holding device for light supply device used for an endoscope and holding a spare light.

An endoscope requires to be supplied with a light, so that there is generally used a light source with a specially large quantity of light such as a halogen lamp. The halogen lamp, however, has so short a life that it must frequently be replaced under normal conditions. Accordingly, it is essential to keep always a spare lamp for replacement at hand.

Generally, in a light supply device of the prior art, the device itself was not provided with a spare lamp. However, very few devices had ones installed therein, though they each were so constructed that a spare lamp was contained in a specially defined space. Consequently, these devices with spare lamps could never be desirable because of their complicated and large-sized structures. Further, the space lamp was each time required to be taken out from the special containing space in its replacement, complicating the replacing operation.

SUMMARY OF THE INVENTION

Accordingly, an object of the present invention is to provide a light supply device for endoscope with a spare lamp having a simple structure so designed as to avoid enlargement in size and facilitate replacement of lamps.

In the light supply device of the invention, a space defined on the opposite side to the light emitting side of a socket provided for supporting the lamp in the device may open to the outside through an opening, where there is provided a cover hinge-coupled to a frame of the device so that it may swing from the closed position to the open position to open the opening. On the inner surface of the cover is attached a holder to which a spare lamp for replacement may be removably fitted.

In the normal condition where the cover is in the closed position, the spare lamp may be contained easily in said space leaving extra room. Meanwhile, when the cover is opened, the spare lamp is moved outward along with the cover, so that an operator may remove quickly the lamp to be replaced from the socket, inserting his hand into the space through the opening. Further, the spare lamp is positioned outward enough to be removed easily from the holder, expediting the lamp replacing operation substantially.

Moreover, in the device of the present invention, the lamp socket is attached to the frame of the device at one edge of the opening and the lamp in use is positioned directed toward the spare lamp within the space. Thus, the containing space in the device may be minimized, enabling miniaturization of the whole device.

Furthermore, in the device of the invention, an angular U-shaped resilient wire is used as a means for fitting the spare lamp to the back of the cover through the holder and the wire may easily be engaged or disengaged from the flanges of the lamp by an operator's manual operation. Accordingly, the spare lamp may easily be removed from and fitted to the holder, improving the efficiency of lamp handling operation. In addition, the use of the wire may simplify the construction of the fitting means.

DETAILED DESCRIPTION OF THE PREFERRED EMBODIMENT

Figure 1:
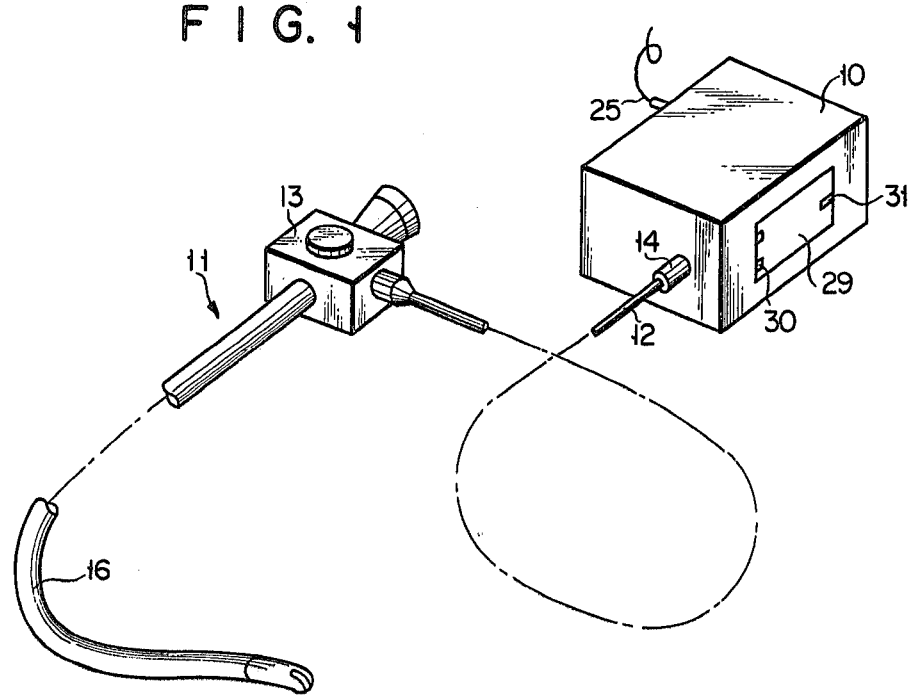
FIG. 1 is a perspective view of the light supply device of the present invention connected to a conventional endoscope in the normal working conditions.

Referring to FIG. 1, the light supply device 10 of the invention is connected to an endoscope 11 by a connecting cord 12. One end of the cord 12 is fixed to a control section 13 of the endoscope 11, while the other end is attached removably tp a connecting socket 14 of the device 10. While in operation. a required quantity of light is transmitted from the device 10 to the control section 13 through a light guide fiber bundle 15 (FIG. 2) in the cord 12, and emitted from the tip end of a flexible tube 16 of the endoscope 11 through a fiber bundle in the tube 16, and illuminates a required region of e.g. a human body cavity with the tube placed in the body cavity. Since the endoscope 11 and connecting cord 12 have conventional constructions, they will not further be described hereinafter.

Figure 3:
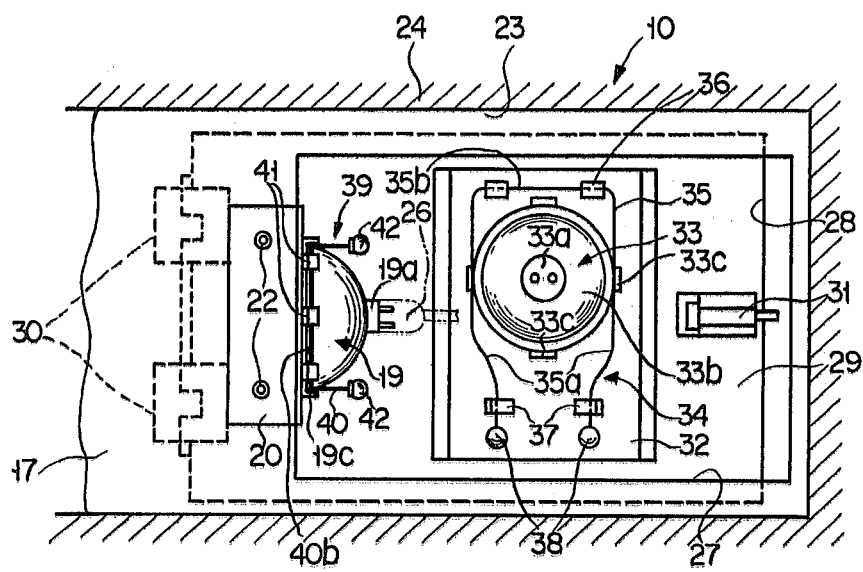
FIG. 3 is a cross sectional view of the device of FIG. 2 as taken along line 3—3.
Figure 2:
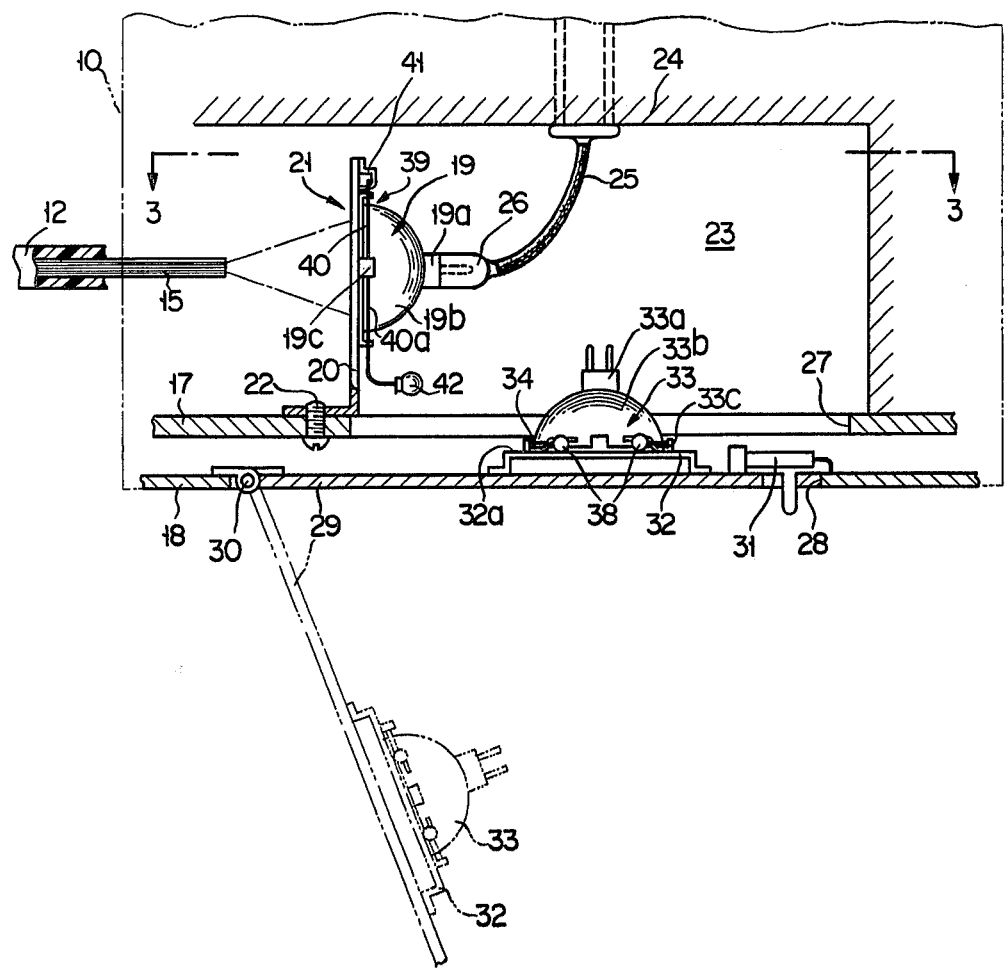
FIG. 2 is an enlarged cross sectional view of the principal part of the device of the present invention as shown in FIG. 1.

Referring now to FIGS. 2 and 3, the light supply device 10 of the present invention includes a base plate 17 and an outer member 18, said plate 17 and member 18 comprising a casing of the device 10.

In the device 10, there is provided a light source section 21 comprising a lamp 19 and a socket 20 to support said lamp 19 toward which the fiber 15 of the connecting cord 12 is extending. A conventional halogen lamp is used for the lamp 19. The light from the lamp 19, as indicated by dot-and-dash line of FIG. 2, is converged, applied to the end face of the fiber bundle 15, and then fed into the bundle 15 through said end face.

The socket 20 is fixed to the base plate 17 by means of bolts 22 with the lamp mounting section of said socket 20 held substantially perpendicular to the base plate. The lamp 19 is attached to the socket 20 at the left side of the socket 20 as regards FIG. 2 or the opposite side to the light emitting side. The constructions of the socket at the lamp mounting portion and the halogen lamp 19 itself may, however, be conventional ones, and so they are shown only briefly in the figure.

Inside the device 10, a space 23 with a fixed area is so defined as to be adjacent to the light source section 21 on the opposite side of the light emitting side of the socket 20. A power cord 25 (FIGS. 1 and 2) connected to an external power source (not shown) extends through the space 23 from a wall 24 defining the space 23, a plug 26 at the extended end of the cord is fitted in with a jack section 19a of the lamp 19, and said lamp 19 is electrically connected to the power source.

The space 23 may communicate with the outside by a rectangular opening 27 formed in the base plate 17 and another rectangular opening 28 formed in the outer casing member 18 at a position substantially directed toward said opening 27. The outer opening 28 is provided with a cover 29. One side edge of the cover 29 is coupled swingably to the outer casing member 18 at one end of the opening 28 by means of hinges 30. The closed position of the cover 29 is as indicated by the full line in FIG. 2, where the opening 28 is closed completely; i.e. the space 23 is isolated from the outside. Meanwhile, the open position of the cover 29 is as indicated by the chain line where the opening 28 is opened to its full and an operator is allowed to put his hand into the space 23 from the outside for removing or mounting of the lamp 19. The angle of swing of the cover 29 may be set optionally, while FIG. 2 shows only one instance of the open position.

The cover 29 in the closed position is locked by means of a lock 31 attached thereto. Since lock 31 is of a conventional construction, it is shown only schematically in the figures.

A holder 32 is fixed to the inside of the cover 29 at the approximate central portion thereof. The holder 32 is formed from a pressed plate material, while, as may be seen from FIG. 2, a holder surface 32a to attach and detach a spare lamp 33 is rendered parallel with the inner surface of the cover 29 in a considerably offset manner when the holder 32 is fixed to the cover 29.

The spare lamp 33 for replacement is removably fitted to said holder 32. As shown fully in FIG. 3, a fitting mechanism 34 comprising a fitting means to fit the spare lamp 33 to the holder 32 comprises a substantially angular U-shaped resilient wire 35, support lugs 36 for supporting rockably a base section 35b to connect both leg sections 35a of the wire with each other on the holder 32, and engaging ears 37 engaging with the respective leg sections 35a of the wire. Further, knobs 38 are fixed at the free ends of the respective leg sections 35a. Each knob 38 may be operated manually by an operator.

The spare lamp 33, taking the same form as the lamp 19 has a shade section 33b. Four circumferentially separated engaging tongues or flanges 33c are formed on the bottom periphery of the section 33b. As shown in FIG. 3, the spare lamp is mounted on the holder 32 with two out of the four flanges 33c engaged with the respective leg sections 35a of the resilient wire 35 as well as the spare lamp 33 is mounted on the holder 32 with said leg sections 35a in engagement with the corresponding ears 37. Both leg sections 35a of the resilient wire 35 have a tendency to move resiliently in opposite directions to each other by their own spring tension. Therefore, even if the cover 29 swings, the spare lamp 33 will never slip off the holder 32 so long as the leg sections 35a are engaged with their respective flanges 33c. In removing the spare lamp 33 from the holder 32, the leg sections 35a are removed from their respective ears 37 and then disengaged from the flanges 33c by swinging the leg sections 35a upwards about the base section 35b. Such fitting and removal of the spare lamp 33 may be accomplished easily by an operator's manual operation of the knobs 38.

The lamp 19 is held on the socket 20 by a lamp holding mechanism 39 similar to the aforementioned fitting mechanism 34 for the spare lamp 33. This lamp holding mechanism 39 is comprised of a substantially angular U-shaped resilient wire 40 and supports lugs 41 for supporting rockably a base section 40b to connect both leg sections 40a of the wire with each other on the socket 20. The leg sections 40a of the resilient wire 40 have a tendency to move resiliently in opposite directions to each other by their own spring tension. In the same manner as the case of the fitting mechanism 34 for the spare lamp 33, the lamp 19 may be held on the socket 20 by engaging the leg sections 40a with flanges 19c formed along the peripheral bottom of a shade section 19b of the lamp as shown in FIGS. 2 and 3. In removing the lamp 19 from the socket 20, an operator grasps respective knobs 42 at the free ends of the leg sections 40a and then swings the leg sections 40a about the base section 40b until the leg sections 40a come off their corresponding flanges 19c. Since the free end portions of the leg sections 40a are bent in a direction away from the socket 20, the knobs 42 are easy for an operator to grasps.

As shown in FIG. 2, the socket 20 is fixed to the base plate 17 at the front edge of the opening 27. The holding mechanism 34 is provided on the inner surface of the cover 29 at a portion near the rear edge of the opening 27. The lamp 19 in use and the spare lamp 33 are disposed perpendicular to each other such that the space 23 is utilized effectively without any interference between the two lamps 19 and 33.

When the lamp 19 has run out, it is replaced in the following manner. First, the lock 31 is released to open the cover 29 as indicated by the chain line in FIG. 2, and the plug 26 is pulled off the jack 19a of the lamp 19 by an operator's hand inserted in the space 23 through the openings 28 and 27. Then, the holding mechanism 39 is released and the lamp 19 is removed from the socket and taken out of the device. Thereafter, the spare lamp 33 is removed from the holder 32 by releasing the fitting mechanism 34, attached to the socket 20, and held in position by the holding mechanism 39. When the plug 26 is put on the jack 33a of the lamp 33, the lamp 33 is connected to the power source. When a new spare lamp is fitted to the holder 32 and the cover 29 is closed, the device is returned to its original working condition.

In replacing lamps, the spare lamp 33 is taken out of the fitting mechanism 34 after the cover 29 has been opened. That portion of the space 23 which has been occupied by the spare lamp 33 is evacuated to allow an operator to freely put his hand into the space 23. That is, the space 23 may be used as a space for lamp replacing operation as well as a space for receiving the spare lamp 33. Accordingly, there is no necessity of providing any special space to receive the spare lamp in the device. The light supply device according to the present invention is not limited to the construction of the embodiment described herein and various changes and modifications of such embodiment may be effected without departing from the scope or spirit of the invention. For instance, the socket 20 may be so constructed as to be fixed directly to the outer casing member 18. It is to be understood that, in this modified embodiment, there will be required only one opening 28 defined in the outer casing member 18. Further, the holder 32 may be formed integrally with the cover 29 by depressing a part of the cover 29 inwards to form a protrusion.

What is claimed is:

1. In a light supply device for an endoscope including a casing;
a chamber formed in said casing;
a light guide bundle, one end of which is mounted in one side wall of the casing to be disposed in the chamber; and
a first holding means for holding a lamp in use to cause the lamp to be disposed adjacent to said one side wall of the casing in the chamber and emit light to said one end of the bundle;
a spare lamp holding device comprising a cover hinged to another side wall of the casing, and normally covering an opening formed in said other side wall of the chamber to communicate with the chamber; and a second holding means provided on the inner surface of the cover and holding a spare lamp at that portion of the chamber which is located opposite to said one side wall with respect to the first holding means and where the spare lamp is not brought into contact with the lamp in use when the cover is closed, said spare lamp being pulled out of the chamber when the cover is opened.

2. In a light supply device according to claim 1, wherein said second holding means comprises a resilient wire engageable with flanges formed on the periphery of the spare lamp, support lugs provided on the inner surface of the cover to swingably support the wire, and engaging ears provided on the inner surface of the cover and engageable with the wire to set the spare lamp in position in the chamber when the wire is engaged by the ears.

3. In a light supply device according to claim 2, wherein said resilient wire is formed in an angular U-shaped configuration.

* * * * *